United States Patent [19]

Iwao et al.

[11] 4,386,096
[45] May 31, 1983

[54] ANTIHYPERTENSIVE 4-THIAZOLIDINECARBOXYLIC ACIDS (FURYL AND THIENYL DERIVATIVES)

[75] Inventors: Junichi Iwao, Takarazuka; Masayuki Oya, Osaka; Toshio Baba, Suita; Tadashi Iso, Tondabayashi; Takehisa Chiba, Kyoto, all of Japan

[73] Assignee: Santen Pharmaceutical Co., Ltd., Osaka, Japan

[21] Appl. No.: 239,601

[22] Filed: Mar. 2, 1981

Related U.S. Application Data

[62] Division of Ser. No. 23,397, Mar. 23, 1979.

[30] Foreign Application Priority Data

| | | | |
|---|---|---|---|
| Apr. 8, 1978 | [JP] | Japan | 53-41632 |
| Apr. 25, 1978 | [JP] | Japan | 53-49657 |
| Jul. 3, 1978 | [JP] | Japan | 53-81116 |

[51] Int. Cl.$^3$ ................ C07D 277/04; A61K 31/425
[52] U.S. Cl. .................................... 424/270; 548/200; 548/201
[58] Field of Search ................ 548/200, 201; 424/270

[56] References Cited

U.S. PATENT DOCUMENTS 4,282,235  8/1981  Ondetti .......................... 424/270

FOREIGN PATENT DOCUMENTS

| | | |
|---|---|---|
| 868532 | 6/1978 | Belgium . |
| 2828578 | 6/1978 | Fed. Rep. of Germany . |
| 54-12372 | 1/1979 | Japan . |
| 54-32466 | 3/1979 | Japan . |
| 2000508A | 1/1979 | United Kingdom . |

*Primary Examiner*—Nicholas S. Rizzo
*Attorney, Agent, or Firm*—Frishauf, Holtz, Goodman & Woodward

[57] ABSTRACT

Derivatives of 4-thiazolidinecarboxylic acid which have the general formula

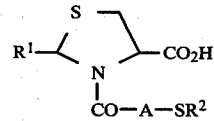

are useful in compositions as antihypertensive agents.

19 Claims, No Drawings

ANTIHYPERTENSIVE 4-THIAZOLIDINECARBOXYLIC ACIDS (FURYL AND THIENYL DERIVATIVES)

This is a division of application Ser. No. 23,397 filed Mar. 23, 1979.

DETAILED DESCRIPTION OF THE INVENTION

This invention relates to derivatives of 4-thiazolidinecarboxylic acid and salts thereof which are useful as antihypertensive agents. These compounds are represented by the formula

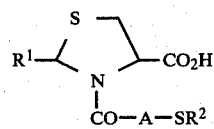

wherein $R^1$ is mercapto-lower alkyl, acylmercapto-lower alkyl, higher alkyl, cycloalkyl, aralkyl, phenyl, furyl, thienyl, pyridyl, naphthyl, substituted higher alkyl, substituted cycloalkyl, substituted aralkyl, substituted phenyl, substituted furyl, substituted thienyl, substituted pyridyl or substituted naphthyl wherein the substituent(s) is lower alkyl, hydroxy, mercapto, lower alkoxy, lower alkylenedioxy, acyloxy, acylmercapto, halogen, nitro, amino, lower alkylamino, acylamino or carboxy;

$R^1$ may be benzofuryl, benzothienyl, indolyl, substituted benzofuryl, substituted benzothienyl or substituted indolyl wherein the substituent(s) is lower alkyl, hydroxy, mercapto, lower alkoxy, lower alkylenedioxy, acyloxy, acylmercapto, halogen, nitro, amino, lower alkylamino, acylamino or carboxy; the substituent(s) may be hydroxy-lower alkyl;

$R^2$ is hydrogen or benzoyl;

A is straight or branched alkylene with 1 to 3 carbon atoms (e.g. —CH$_2$—, —CH(CH$_3$)—, —CH$_2$CH$_2$—, —CH(CH$_3$)CH$_2$—); in the formula lower alkyl or alkylene is saturated or unsaturated, straight or branched chain with 1 to 6 carbon atoms;

higher alkyl is saturated or unsaturated, straight or branched chain with 7 to 20 carbon atoms;

acyl is acetyl, pivaloyl, substituted or unsubstituted benzoyl, benzyloxycarbonyl, etc.;

aralkyl is benzyl, etc.; and salts thereof. The same shall be applied hereinafter.

The compounds of formula I of this invention are mercaptoacylamino acids and S-substituted mercaptoacylamino acids. Mercaptoacylamino acids have an inhibitory activity against angiotensin I-converting enzyme and therefore they are useful as antihypertensive agents. S-Substituted mercaptoacylamino acids release mercaptoacylamino acid by enzymatic and/or chemical cleavage when administered to men or animals.

The compounds of formula I can be produced by the following methods.

An acid of the formula

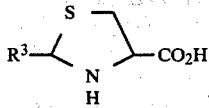

is reacted with an alkanoic acid or an alkanoyl halide of the formula

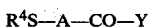

by one of the known procedures wherein the compound III is activated prior to reaction with the acid II, forming a mixed anhydride, symmetrical anhydride, acid chloride, active ester, etc. to produce the compounds of the formula I. The resulting compound can then be converted to the compound of formula I, wherein $R^2$ is hydrogen, by hydrolysis or reduction (e.g. acid treatment with hydrochloric acid, p-toluenesulfonic acid, etc.; alkali treatment with sodium hydroxide, ammonia, etc.; catalytic reduction with palladium-carbon, etc.; alkali metal treatment in liquid ammonia).

In another way, the compounds of formula I are produced by reacting an acid of formula II with a haloalkanoic acid or a haloalkanoyl halide of the formula

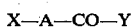

and by reacting the resulting haloacid of the formula

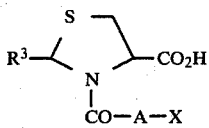

with thiobenzoic acid or benzylmercaptan. The resulting compound can then be converted to the compound of formula I, wherein $R^2$ is hydrogen, by hydrolysis or reduction in the same manner as above. In the formulas, $R^3$ is acylmercapto-lower alkyl, higher alkyl, cycloalkyl, aralkyl, phenyl, furyl, thienyl, pyridyl, naphthyl, substituted higher alkyl, substituted cycloalkyl, substituted aralkyl, substituted phenyl, substituted furyl, substituted thienyl, substituted pyridyl or substituted naphthyl wherein the substituent(s) is lower alkyl, hydroxy, lower alkoxy, lower alkylenedioxy, acyloxy, acylmercapto, halogen, nitro, lower alkylamino, acylamino or carboxy; the substituent(s) may be hydroxy-lower alkyl;

$R^4$ is benzoyl or benzyl;

$R^4$ may be alkyl- or phenylcarbamoyl;

X is halogen (e.g. bromine or chlorine);

Y is hydroxy or halogen.

The compounds of formula I synthesized by the above methods can form the conventional salts to be generally used as medicine such as sodium salt, potassium salt, calcium salt, aluminum salt, ammonium salt, diethylamine salt, triethanolamine salt, etc.

The compounds of formula I have the stereoisomers which are within the limit of this invention because they have one or more asymmetric carbon atoms. The NMR spectrum (DMSO-d$_6$) of 3-(S-benzoyl-3-mercaptopropanoyl)-2-phenyl-4-thiazolidinecarboxylic acid (Compound 15) at 23° C. has one pair of signals of C(4)-methine proton at 5.45 ppm (dd, J=4.0, 6.0 Hz) and 4.84 ppm (dd, J=7.5, 8.0 Hz) and another pair of signals of C(2)-methine proton at 6.46 ppm (singlet) and 6.26 ppm (singlet), while at 100° C. the signal of C(4)-methine proton at 5.00 ppm (dd, J=5.0, 6.0 Hz) and the signal of C(2)-methine proton at 6,32 ppm (singlet). This compound has the same spectrum pattern as (2R, 4R)-3-acetyl-2-phenyl-4-thiazolidinecarboxylic acid of which the configuration was determined by R. Parthasarathy et al. [J. Am. Chem. Soc., 98, 6634 (1976)]. Therefore the configuration of Compound 15 proved to be (2R, 4R). In Tables I and II, "a" and "b" of Compd. No. represent diastereoisomers that one configuration is (2R, 4R) and another is (2S, 4R).

Examples are shown below, although this invention is not limited to these examples.

EXAMPLE 1

(4R)-3-[(2S)-S-Benzoyl-3-mercapto-2-methyl-propanoyl]-2-(4-methylphenyl)-4-thiazolidinecarboxylic acid (Compound 21)

4.5 g of (4R)-2-(4-methylphenyl)-4-thiazolidinecarboxylic acid and 4.3 g of sodium carbonate are dissolved in 25 ml of water and 4.9 g of (2S)-S-benzoyl-3-mercapto-2-methylpropanoyl chloride is added dropwise while stirring under ice-cooling. After the addition, the mixture is stirred under ice-cooling for 1 hour and acidified with dilute hydrochloric acid. The produced oil is extracted with ethyl acetate. The ethyl acetate layer is washed with saturated sodium chloride solution, dried over anhydrous sodium sulfate, and concentrated to dryness in vacuo to give oil. The produced oil is purified by silica gel column chromatography to give the titled compound, yield 4.0 g (48%), mp. 131°–132° C. (ethyl acetatehexane), $[\alpha]_D^{26}+117.6°$ (c=1.0, methanol).

IR (nujol, cm$^{-1}$) 1755, 1650, 1610, 915.

Analysis ($C_{22}H_{23}NO_4S_2$): Calcd: C, 61.52; H, 5.40; N, 3.26. Found: C, 61.60; H, 5.42; N, 3.26.

EXAMPLE 2

(4R)-3-(S-Benzoyl-3-mercaptopropanoyl)-2-(2-hydroxyphenyl)-4-thiazolidinecarboxylic acid (Compound 45)

11.3 g of (4R)-2-(2-hydroxyphenyl)-4-thiazolidinecarboxylic acid and 13.2 g of triethylamine are dissolved in 200 ml of dehydrated acetone and 11.7 g of S-benzoyl-3-mercaptopropanoyl chloride is added dropwise while stirring under ice-cooling. After the addition, the mixture is stirred under ice-cooling for 1 hour. 4 N Hydrochloric acid in ether is added to this mixture and the precipitate is filtered. The filtrate is concentrated in vacuo and the obtained oil is dissolved in ethyl acetate, washed with 2 N hydrochloric acid and saturated sodium chloride solution, dried over anhydrous sodium sulfate, and concentrated to dryness in vacuo to give the titled compound, yield 12 g (58%), mp. 100.5°–101° C. (dec.) (ethyl acetatebenzene), $[\alpha]_D^{26}+130.8°$ (c=1.0, methanol).

IR (nujol, cm$^{-1}$) 3460, 1760, 1663, 1580, 910.

Analysis ($C_{20}H_{19}NO_5S_2 \cdot C_6H_6$): Calcd: C, 63.01; H, 5.08; N, 2.83. Found: C, 63.01; H, 5.07; N, 2.61.

EXAMPLE 3

(4R)-3-(S-Benzoyl-3-mercaptopropanoyl)-2-(2-thienyl)-4-thiazolidinecarboxylic acid (Compound 88)

10.8 g of (4R)-2-(2-thienyl)-4-thiazolidinecarboxylic acid and 10.6 g of sodium carbonate are dissolved in 100 ml of water and 8.6 g of 3-bromopropanoyl chloride is added dropwise while stirring under ice-cooling. After the addition, the mixture is stirred under ice-cooling for 2 hours. To this reaction solution, 8.8 g of potassium thiobenzoate is added and stirred at room temperature for 1 hour. The solution is acidified with dilute hydrochloric acid and the produced oil is extracted with ethyl acetate. The ethyl acetate layer is washed with saturated sodium chloride solution, dried over anhydrous sodium sulfate, and concentrated in vacuo to give the titled compound, yield 11.6 g (57%), mp. 141°–143° C. (benzene), $[\alpha]_D^{25}+107.7°$ (c=1.0, methanol).

IR (nujol, cm$^{-1}$) 1745, 1645, 1610, 917.

Analysis ($C_{18}H_{17}NO_4S_3$): Calcd: C, 53.05; H, 4.20; N, 3.44. Found: C, 52.93; H, 4.01; N, 3.31.

EXAMPLE 4

(4R)-3-[(2S)-S-Benzoyl-3-mercapto-2-methyl-propanoyl]-2-(2-thienyl)-4-thiazolidinecarboxylic acid (Compound 90)

11.2 g of (2S)-S-benzoyl-3-mercapto-2-methylpropanoic acid and 5.1 g of triethylamine are dissolved in 100 ml of dehydrated tetrahydrofuran. To this solution, 6.8 g of isobutyl chloroformate is added dropwise while stirring at the temperature maintained −5° C. After the addition, the mixture is stirred at room temperature for 10 minutes. To this solution, 10.8 g of (4R)-2-(2-thienyl)-4-thiazolidinecarboxylic acid and 5.1 g of triethylamine dissolved in the mixed solution of 5 ml of tetrahydrofuran and 15 ml of water are added. The mixture is stirred at room temperature for 30 minutes. To this reaction mixture, 200 ml of water is added and the mixture is extracted with ethyl acetate. The aqueous layer is acidified with dilute hydrochloric acid and the produced oil is extracted with ethyl acetate. The ethyl acetate layer is washed with water, dried over anhydrous sodium sulfate, and concentrated in vacuo to give the titled compound, yield 10.3 g (49%), mp. 136°–137° C. (benzene), $[\alpha]_D^{25}+79.6°$ (c=1.0, methanol).

IR (nujol, cm$^{-1}$) 1750, 1650, 1620, 920

Analysis ($C_{19}H_{19}NO_4S_3$): Calcd: C, 54.14; H, 4.54; N, 3.32. Found: C, 54.19; H, 4.36; N, 3.26.

EXAMPLE 5

(4R)-2-(2-Hydroxyphenyl)-3-(3-mercaptopropanoyl)-4-thiazolidinecarboxylic acid (Compound 46)

To 4.2 g of (4R)-3-(S-benzoyl-3-mercaptopropanoyl)-2-(2-hydroxyphenyl)-4-thiazolidinecarboxylic acid, 40 ml of conc. ammonia is added and this solution is stirred at room temperature for 1 hour. Excess ammonia is removed in vacuo and the by-product, benzamide, is extracted with ethyl acetate. The aqueous layer is acidified with dilute hydrochloric acid and the produced oil is extracted with ethyl acetate. The ethyl acetate layer is washed with water, dried over anhydrous sodium sulfate, and concentrated to dryness in vacuo to give the titled compound, yield 2.2 g (70%), mp. 146°–148° C. (ethyl acetate), $[\alpha]_D^{26}+176°$ (c=1.0, methanol).

IR (nujol, cm$^{-1}$) 3390, 1724, 1620.

Analysis ($C_{13}H_{15}NO_4S_2$): Calcd: C, 49.82; H, 4.82; N, 4.47. Found: C, 49.74; H, 4.88; N, 4.32.

Tables I, II and III show various compounds and physical constants including the compounds specified in the examples.

TABLE I

[Structure: compound with CO₂H, SR² groups, and N, S-containing ring with R¹, R⁵ substituents]

| Compd. No. | R¹ | R⁵ | R² | Method of prepn. (Examp. No.) | Yield (%) | mp. (°C.) | Recrystn. solvent | [α]D deg. (c, solv., °C.) | Formula | Analysis (%) Calcd. (Found) C | H | N |
|---|---|---|---|---|---|---|---|---|---|---|---|---|
| 1 | Me₂C=... (Me, Me group with chain) | Me | COPh | 2 | 84 | oil | | −104.3 (1.0, MeOH, 25) | C₂₄H₃₃NO₄S₂ | | | |
| | | | | | | 119−120 | c-hexane | −61.1 (1.0, MeOH, 25) | C₂₄H₃₃NO₄S₂·C₁₂H₂₃N* | 67.04 (67.21) | 8.75 (8.84) | 4.34 (4.31) |
| 2 | (similar Me,Me group) | Me | H | 5 | 66 | oil | | −68.5 (1.1, MeOH, 25) | C₁₇H₂₉NO₃S₂ | | | |
| 3 | cyclohexyl (H) | Me | COPh | 2 | 81 | oil | | −56.5 (1.0, MeOH, 25) | C₂₁H₂₇NO₄S₂ | | | |
| | | | | | | 128−133.5 | EtOH—ether | | C₂₁H₂₇NO₄S₂·C₁₂H₂₃N* | 65.74 (65.85) | 8.36 (8.41) | 4.65 (4.59) |
| 4 | cyclohexyl (H) | Me | H | 5 | 76 | amorph. | | −72.2 (1.0, MeOH, 25) | C₁₄H₂₃NO₃S₂ | | | |
| 5a | (CH₂)₂SAc | H | COPh | 2 | 27 | oil | | −79.1 (1.0, MeOH, 25) | C₁₈H₂₁NO₅S₃ | | | |
| | | | | | | 186−188 | EtOH | | C₁₈H₂₁NO₅S₃·C₁₂H₂₃N* | 59.18 (59.05) | 7.28 (7.28) | 4.60 (4.56) |
| 5b | (CH₂)₂SAc | H | COPh | 2 | 23 | oil | | −33.3 (1.0, MeOH, 25) | C₁₈H₂₁NO₅SO₃ | | | |
| | | | | | | 112−114 | EtOAc | | C₁₈H₂₁NO₅S₃·C₁₂H₂₃N* | 59.18 (59.01) | 7.28 (7.25) | 4.60 (4.53) |
| 6a | (CH₂)₂SH | H | H | 5 | 63 | 138−141.5 | EtOAc | −166.3 (1.0, MeOH, 25) | C₉H₁₅NO₃S₃ | 38.41 (38.57) | 5.37 (5.32) | 4.98 (4.92) |
| 6b | (CH₂)₂SH | H | H | 5 | 52 | 97.5−102.5 | | −52.6 (1.0, MeOH, 25) | C₉H₁₅NO₃S₃ | | | |
| 7a | (CH₂)₂SAc | Me | COPh | 2 | 21 | oil | | −99.3 | C₁₉H₂₃NO₅S₃ | | | |
| | | | | | | 178.5−189 | | | C₁₉H₂₃NO₅S₃·C₁₂H₂₃N* | 59.78 | 7.44 | 4.50 |

TABLE I-continued

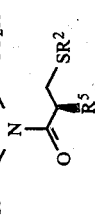

| Compd. No. | R[1] | R[5] | R[2] | Method of prepn. (Examp. No.) | Yield (%) | mp. (°C.) | Recrystn. solvent | $[\alpha]_D$ deg. (c, solv., °C.) | Formula | Analysis (%) Calcd. (Found) C | H | N |
|---|---|---|---|---|---|---|---|---|---|---|---|---|
| 7b | (CH$_2$)$_2$SAc | Me | COPh | 2 | | oil | | | C$_{19}$H$_{23}$NO$_5$S$_3$ | (59.72) | (7.43) | (4.45) |
| | | | | | | 157-158 | EtOh—ether | −70.6 (1.0, MeOH, 25) | C$_{19}$H$_{23}$NO$_5$S$_3$·C$_{12}$H$_{23}$N* | 59.78 (59.66) | 7.44 (7.45) | 4.50 (4.43) |
| 8a | (CH$_2$)$_2$SH | Me | H | 5 | 75 | 141-142 | EtOAc | −175.4 (1.0, MeOH, 25) | C$_{10}$H$_{17}$NO$_3$S$_3$·¼C$_4$H$_8$O$_2$** | 41.62 (41.31) | 6.03 (5.82) | 4.41 (4.71) |
| 8b | (CH$_2$)$_2$SH | Me | H | 5 | 71 | oil | | −117.5 (1.0, MeOH, 25) | C$_{10}$H$_{17}$NO$_3$S$_3$ | | | |
| 9a | CH$_2$Ph | Me | COPh | 2 | 38 | 190 dec. | EtOAc | −113.2 (1.3, MeOH, 28) | C$_{22}$H$_{23}$NO$_4$S$_2$ | | | |
| 9b | CH$_2$Ph | Me | COPh | 2 | 30 | 148.5-149.5 | EtOAc—c-hexane | −147.8 (1.2, MeOH, 28) | C$_{22}$H$_{23}$NO$_4$S$_2$ | 61.52 (61.55) | 5.40 (5.42) | 3.26 (3.27) |
| 10a | CH$_2$Ph | Me | H | 5 | 85 | 159-161 | EtOAc | −97.6 (0.5, MeOH, 25) | C$_{15}$H$_{19}$NO$_3$S$_2$ | | | |
| 10b | CH$_2$Ph | Me | H | 5 | 74 | amorph. | | −151.0 (1.0, MeOH, 25) | C$_{15}$H$_{19}$NO$_3$S$_2$ | | | |

*C$_{12}$H$_{23}$N is dicyclohexylamine.
**C$_4$H$_8$O$_2$ is ethyl acetate.

TABLE II

[Structure: benzothiazine with S, N, phenyl with R6, CH(CO2H)CH2—N—C(=O)—CR5(H)—(CH2)n—SR2]

| Compd. No. | R6 | R5 | R2 | n | Method of prepn. (Examp. No.) | Yield (%) | mp. (°C.) | Recrystn. solvent | [α]D deg. (c, solv., °C.) | Formula | Analysis (%) Calcd. (Found) C | H | N |
|---|---|---|---|---|---|---|---|---|---|---|---|---|---|
| 11 | H | H | COPh | 0 | 1 | 78 | 134–135.5 | THF—ether | +126.0 (1.0, MeOH, 25) | C19H17NO4S2 | 58.90 (59.14) | 4.42 (4.38) | 3.61 (3.56) |
| 12 | H | H | H | 0 | 5 | 85 | 142–143.5 | EtOAc | +121.0 (1.2, MeOH, 25) | C12H13NO3S2 | 50.87 (51.11) | 4.62 (4.58) | 4.94 (4.80) |
| 13a | H | Me | COPh | 0 | 1 | 33 | 186–186.5 | EtOAc | +162.1 (1.0, DMF, 25) | C20H19NO4S2 | 59.83 (59.77) | 4.77 (4.80) | 3.49 (3.50) |
| 13b | H | Me | COPh | 0 | 1 | 31 | 106–116 | EtOAc—c-hexane | +104.9 (1.0, DMF, 25) | C20H19NO4S2 | 59.83 (59.99) | 4.77 (4.75) | 3.49 (3.41) |
| 14a | H | Me | H | 0 | 5 | 85 | 173–175 | EtOAc | +106.8 (1.0, DMF, 25) | C13H15NO3S2 | 52.51 (52.77) | 5.08 (5.03) | 4.71 (4.65) |
| 15 | H | H | COPh | 1 | 1 | 98 | 126–131 | EtOAc | +110.5 (1.0, MeOH, 25) | C20H19NO4S2·H2O | 57.26 (57.21) | 5.04 (5.08) | 3.34 (3.36) |
| 16 | H | H | H | 1 | 5 | 81 | amorph. | | +104.3 (1.0, MeOH, 25) | C13H15NO3S2 | | | |
| 17 | H | Me | COPh | 1 | 2 4 5 | 68 58 54 | 150–151.5 | benzene-c-hexane | +89.1 (1.3, MeOH, 25) | C21H21NO4S2 | 60.70 (60.93) | 5.09 (5.01) | 3.37 (3.27) |
| 18 | H | Me | H | 1 | 5 | 74 | oil | | +72.2 (0.5, MeOH, 25) | C14H17NO3S2 | | | |
| 19 | 4-Me | H | COPh | 1 | 1 | 55 | 122–129 | EtOAc | +131.4 (1.0, MeOH, 26) | C21H21NO4S2·H2O | 58.18 (58.20) | 5.35 (5.33) | 3.23 (3.28) |
| 20 | 4-Me | H | H | 1 | 5 | 74 | amorph. | | +125.2 (1.0, MeOH, 26) | C14H17NO3S2 | 54.00 (53.81) | 5.50 (5.51) | 4.50 (4.28) |
| 21 | 4-Me | Me | COPh | 1 | 1 | 48 | 131–132 | EtOAc—n-hexane | +117.6 (1.0, MeOH, 26) | C22H23NO4S2 | 61.52 (61.60) | 5.40 (5.42) | 3.26 (3.26) |
| 22 | 4-Me | Me | H | 1 | 5 | 83 | 154–156 | EtOAc—c-hexane | +112.9 (1.0, MeOH, 26) | C15H19NO3S2 | 55.36 (55.23) | 5.88 (5.92) | 4.30 (4.22) |
| 23 | 2-Cl | H | COPh | 1 | 2 | 28 | 160–161 | EtOAc—c-hexane | −58.2 (1.0, MeOH, 26) | C20H18ClNO4S2 | | | |
| 24 | 2-Cl | H | H | 1 | 5 | 86 | 133–134 | EtOAc | −64.6 (1.0, MeOH, 26) | C13H14ClNO3S2 | | | |
| 25 | 4-Cl | H | COPh | 1 | 2 | 51 | 119–131 | EtOAc | +110.0 (1.0, MeOH, 26) | C20H18ClNO4S2·H2O | 52.92 (52.84) | 4.44 (4.42) | 3.09 (3.09) |
| 26 | 4-Cl | H | H | 1 | 5 | 90 | amorph. | | +77.1 (1.0, MeOH, 26) | C13H14ClNO3S2 | | | |
| 27 | 2,4-Cl2 | H | COPh | 0 | 2 | 16 | amorph. | | −187.8 (1.0, MeOH, 26) | C19H15Cl2NO4S2 | | | |
| 28 | 2,4-Cl2 | H | H | 0 | 5 | 29 | amorph. | | −303.8 (0.3, MeOH, 25) | C12H11Cl2NO3S2 | | | |
| 29a | 4-F | Me | COPh | 0 | 2 | 32 | 178–180 | EtOAc | +155.3 | C20H18FNO4S2 | | | |

TABLE II-continued

| Compd. No. | R⁶ | R⁵ | R² | n | Method of prepn. (Examp. No.) | Yield (%) | mp. (°C.) | Recrystn. solvent | [α]$_D$ deg. (c, solv., °C.) | Formula | Analysis (%) Calcd. (Found) C | H | N |
|---|---|---|---|---|---|---|---|---|---|---|---|---|---|
| 29b | 4-F | Me | COPh | 0 | 2 | 18 | amorph. | | (1.0, MeOH, 26) +98.6 | C₂₀H₁₈FNO₄S₂ | | | |
| 30a | 4-F | Me | H | 0 | 5 | 95 | 199-200 | EtOAc | (1.1, MeOH, 26) +92.2 | C₁₃H₁₄FNO₃S₂ | 49.51 (49.56) | 4.47 (4.43) | 4.44 (4.47) |
| 31 | 2-NO₂ | Me | COPh | 1 | 2 | 69 | amorph. | | (1.0, MeOH, 26) −257.0 | C₂₁H₂₀N₂O₆S₂ | | | |
| | | | | | | | 225-226 | MeOH | (0.4, MeOH, 25) −158.0 | C₂₁H₂₀N₂O₆S₂·C₁₂H₂₃N* | 61.75 (61.42) | 6.75 (6.69) | 6.55 (6.41) |
| 32 | 2-NO₂ | Me | H | 1 | 5 | 65 | 118-121 | EtOAc—benzene | (1.0, MeOH, 25) −284.7 | C₁₄H₁₆N₂O₅S₂·½ C₆H₆ | 51.63 (51.47) | 4.84 (4.77) | 7.08 (7.00) |
| 33 | 3-NO₂ | Me | COPh | 1 | 2 | 43 | 128-130 | benzene | (0.4, MeOH, 26) +34.0 | C₂₁H₂₀N₂O₆S₂ | | | |
| 34 | 3-NO₂ | Me | H | 1 | 5 | 55 | 153-154 | EtOAc | (1.0, MeOH, 25) +94.9 | C₁₄H₁₆N₂O₅S₂ | 47.18 (46.82) | 4.52 (4.46) | 7.86 (7.52) |
| 35 | 4-NO₂ | Me | COPh | 1 | 2 | 60 | oil 223-228 | MeOH | (1.0, MeOH, 25) −234.0 | C₂₁H₂₀N₂O₆S₂ C₂₁H₂₀N₂O₆S₂·C₁₂H₂₃N* | | | |
| 36 | 4-NMe₂ | Me | COPh | 1 | 1 | 90 | 138-142 dec. | | (0.6, MeOH, 26) +4.2 | C₂₃H₂₆N₂O₄S₂ | | | |
| 37 | 4-NMe₂ | Me | H | 1 | 5 | 65 | amorph. | | (0.5, MeOH, 25) +121.6 | C₁₆H₂₂N₂O₃S₂ | | | |
| 38 | 4-NHAc | Me | COPh | 1 | 2 | 87 | oil | | (0.9, MeOH, 25) +126.0 | C₂₃H₂₄N₂O₅S₂ | | | |
| 39 | 4-NHAc | Me | H | 1 | 5 | 25 | 169-173 | EtOAc | (1.1, MeOH, 25) +114.3 | C₁₆H₂₀N₂O₄S₂ | | | |
| 40 | 4-NHCO₂CH₂Ph | Me | COPh | 1 | 2 | 53 | oil | | (0.5, MeOH, 25) +171.8 | C₂₉H₂₈N₂O₆S₂ | | | |
| 41 | 2-CO₂H | H | COPh | 1 | 1 | 72 | 115-120 | EtOAc—benzene | (1.0, MeOH, 25) +236.5 | C₂₁H₁₉NO₆S₂·¼ C₆H₆ | 60.76 (60.87) | 4.70 (4.74) | 2.78 (2.80) |
| 42 | 2-CO₂H | H | H | 1 | 5 | 81 | 207-208 dec. | EtOAc—MeOH | (0.6, MeOH, 25) +126.9 | C₁₄H₁₅NO₅S₂ | 49.25 (49.41) | 4.43 (4.45) | 4.10 (4.13) |
| 43 | 2-OH | H | COPh | 0 | 2 | 46 | amorph. | | (1.0, MeOH, 26) +193.4 | C₁₉H₁₇NO₅S₂ | | | |
| 44 | 2-OH | H | H | 0 | 5 | 67 | 156-158 dec. | EtOAc—MeOH | (1.0, MeOH, 26) +130.8 | C₁₂H₁₃NO₄S₂ | 48.15 (47.75) | 4.38 (4.19) | 4.68 (4.53) |
| 45 | 2-OH | H | COPh | 1 | 2 | 58 | 100.5-101 dec. | EtOAc—benzene | (1.0, MeOH, 26) +176.0 | C₂₀H₁₉NO₅S₂·C₆H₆ | 63.01 (63.01) | 5.08 (5.07) | 2.83 (2.61) |
| 46 | 2-OH | H | H | 1 | 5 | 70 | 146-148 | EtOAc | | C₁₃H₁₅NO₄S₂ | 49.82 | 4.82 | 4.47 |

TABLE II-continued

| Compd. No. | R⁶ | R⁵ | R² | n | Method of prepn. (Examp. No.) | Yield (%) | mp. (°C.) | Recrystn. solvent | $[\alpha]_D$ deg. (c, solv., °C.) | Formula | Analysis (%) Calcd. (Found) C | H | N |
|---|---|---|---|---|---|---|---|---|---|---|---|---|---|
| 47 | 2-OH | H | COPh | 2 | 2 | 48 | 111-113 dec. | EtOAc—c-hexane | (1.0, MeOH, 26) +112.1 | $C_{21}H_{21}NO_5S_2 \cdot \frac{1}{4} C_6H_{12}$** | (49.74) (49.92) | (4.88) 6.11 | (4.32) 2.83 |
| 48 | 2-OH | H | H | 2 | 5 | 62 | amorph. | | (1.0, MeOH, 26) +138.4 | $C_{14}H_{17}NO_4S_2$ | (62.15) | (6.08) | (2.59) |
| 49 | 2-OH | Me | COPh | 1 | 2 | 76 | amorph. | | (1.0, MeOH, 26) +118.1 | $C_{21}H_{21}NO_5S_2$ | | | |
| 50 | 2-OH | Me | H | 1 | 5 | 84 | 167-168 dec. | EtOAc | (1.0, MeOH, 26) +160.6 | $C_{14}H_{17}NO_4S_2$ | | | |
| 51 | 3-OCOPh | H | COPh | 1 | 2 | 52 | amorph. | | (1.0, MeOH, 26) +85.1 | $C_{26}H_{23}NO_6S_2$ | | | |
| 52 | 3-OH | H | H | 1 | 5 | 69 | 156-157 | EtOAc—MeOH | (1.0, MeOH, 27) +122.4 | $C_{13}H_{15}NO_4S_2$ | 49.82 (49.66) | 4.82 (4.72) | 4.47 (4.35) |
| 53 | 3-OCOPh | Me | COPh | 1 | 2 | 66 | 131.5-132 dec. | c-hexane acetone | (1.0, MeOH, 26) +86.1 | $C_{27}H_{25}NO_6S_2$ | 61.93 (62.32) | 4.81 (4.45) | 2.67 (2.60) |
| 54 | 3-OH | Me | H | 1 | 5 | 62 | amorph. | | (1.0, MeOH, 26) +73.2 | $C_{14}H_{17}NO_4S_2$ | | | |
| 55 | 4-OCO₂CH₂Ph | H | COPh | 1 | 1 | 69 | 101-104 | EtOAc | (1.0, MeOH, 26) +98.3 | $C_{27}H_{25}NO_7S_2$ | | | |
| 56 | 4-OH | H | H | 1 | 5 | 67 | amorph. | | (1.0, MeOH, 26) +78.5 | $C_{13}H_{15}NO_4S_2$ | | | |
| 57 | 3,4-(OH)₂ | H | COPh | 1 | 1 | 67 | amorph. | | (1.0, MeOH, 27) +117.6 | $C_{20}H_{19}NO_6S_2$ | | | |
| 58 | 3,4-(OH)₂ | H | H | 1 | 5 | 82 | amorph. | | (1.0, MeOH, 26) +104.5 | $C_{13}H_{15}NO_5S_2$ | | | |
| 59 | 2-OH, 5-Cl | Me | COPh | 1 | 2 | 60 | amorph. | | (1.0, MeOH, 25) +108.2 | $C_{21}H_{20}ClNO_5S_2$ | | | |
| 60 | 2-OH, 5-Cl | Me | H | 1 | 5 | 62 | 159-160 dec. | EtOAc—benzene | (1.0, MeOH, 25) +170.7 | $C_{14}H_{16}ClNO_4S_2 \cdot 2/5 C_6H_6$ | 50.11 (50.09) | 4.72 (4.69) | 3.56 (3.35) |
| 61 | 2-OMe | H | COPh | 1 | 2 | 63 | 85-89 | EtOAc | (1.1, MeOH, 25) +139.5 | $C_{21}H_{21}NS_5S_2$ | 58.45 (58.24) | 4.90 (5.21) | 3.25 (2.96) |
| 62 | 2-OMe | H | H | 1 | 5 | 73 | 138-139 | EtOAc | (1.1, MeOH, 25) +186.6 | $C_{14}H_{17}NO_4S_2$ | 51.36 (51.02) | 5.23 (5.16) | 4.28 (4.22) |
| 63 | 2-OMe | Me | COPh | 1 | 2 | 72 | 169-170 | EtOAc | (1.1, MeOH, 25) +130.0 | $C_{22}H_{23}NS_5S_2$ | 59.31 (59.26) | 5.20 (5.18) | 3.14 (3.16) |
| 64 | 2-OMe | Me | H | 1 | 5 | 41 | 145-146 | EtOAc | (1.1, MeOH, 25) +173.8 | $C_{15}H_{19}NO_4S_2$ | 52.77 (52.51) | 5.61 (5.59) | 4.10 (4.12) |
| 65 | 4-OMe | H | H | 1 | 2 | 88 | 114-116 | EtOAc | (1.0, MeOH, 26) +128.3 | $C_{21}H_{21}NO_5S_2 \cdot 3/2 H_2O$ | 55.01 (55.21) | 5.28 (4.98) | 3.05 (3.04) |

TABLE II-continued

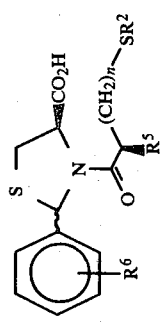

| Compd. No. | R⁶ | R⁵ | R² | n | Method of prepn. (Examp. No.) | Yield (%) | mp. (°C.) | Recrystn. solvent | $[\alpha]_D$ deg. (c, solv., °C.) | Formula | Analysis (%) Calcd. (Found) C | H | N |
|---|---|---|---|---|---|---|---|---|---|---|---|---|---|
| 66 | 4-OMe | H | H | 1 | 5 | 88 | oil | | +92.3 (0.9, MeOH, 25) | $C_{14}H_{17}NO_4S_2$ | | | |
| 67 | 4-OMe | Me | COPh | 1 | 2 | 81 | oil | | +109.8 (0.8, MeOH, 25) | $C_{22}H_{23}NO_5S_2$ | | | |
| | | | | | | | | acetone-ether | +85.6 (1.1, MeOH, 25) | $C_{22}H_{23}NO_5S_2 \cdot C_{12}H_{23}N^*$ | | | |
| 68 | 4-OMe | Me | H | 1 | 5 | 85 | 139-140 | EtOAc | +120.3 (1.0, MeOH, 25) | $C_{15}H_{19}NO_4S_2$ | 52.77 (52.44) | 5.61 (5.51) | 4.10 (4.03) |
| 69 | 3,4-(OMe)₂ | H | COPh | 1 | 2 | 55 | oil | | +154.0 (1.0, MeOH, 25) | $C_{22}H_{23}NO_6S_2$ | | | |
| 70 | 3,4,5-(OMe)₃ | Me | COPh | 1 | 2 | 89 | amorph. | | +130.5 (1.0, MeOH, 24) | $C_{24}H_{27}NO_7S_2$ | | | |
| 71 | 3,4,5-(OMe)₃ | Me | H | 1 | 5 | 31 | amorph. | | +115.0 (1.5, MeOH, 24) | $C_{17}H_{23}NO_6S_2$ | | | |
| 72 | 2-OH, 3-OMe | H | COPh | 1 | 2 | 55 | 135-137 | benzene | +132.2 (1.0, MeOH, 28) | $C_{21}H_{21}NO_6S_2 \cdot 1/5 \; C_6H_6$ | 57.57 (57.36) | 4.83 (4.81) | 3.02 (2.82) |
| 73 | 2-OH, 3-OMe | H | H | 1 | 5 | 78 | amorph. | | +144.5 (1.0, MeOH, 28) | $C_{14}H_{17}NO_5S_2$ | | | |
| 74 | 2-OH, 4-OMe | H | COPh | 1 | 2 | 72 | amorph. | | +54.6 (1.0, MeOH, 24) | $C_{21}H_{21}NO_6S_2$ | | | |
| 75 | 2-OH, 4-OMe | H | H | 1 | 5 | 82 | 134-135 | acetone-benzene | +179.0 (1.1, MeOH, 24) | $C_{14}H_{17}NO_5S_2$ | | | |
| 76 | 2-OH, 4-OMe | Me | COPh | 1 | 2 | 82 | 152 dec. | benzene-ether | +163.2 (0.9, MeOH, 25) | $C_{22}H_{23}NO_6S_2$ | | | |
| 77 | 2-OH, 4-OMe | Me | H | 1 | 5 | 68 | 147-148 | EtOAc | +146.2 (1.0, MeOH, 24) | $C_{15}H_{19}NO_5S_2$ | 50.40 (50.68) | 5.36 (5.69) | 3.92 (3.53) |
| 78 | 4-OH, 3-OMe | Me | COPh | 1 | 2 | 63 | amorph. | | +96.0 (1.1, MeOH, 26) | $C_{27}H_{31}NO_7S_2$ | | | |
| 79 | 4-OH, 3-OMe | Me | H | 1 | 5 | 62 | amorph. | | +104.7 (1.0, MeOH, 26) | $C_{15}H_{19}NO_5S_2$ | | | |
| 80 | 3,4-OCH₂O— | Me | COPh | 1 | 2 | 98 | amorph. | | +98.8 (1.0, MeOH, 25) | $C_{22}H_{21}NO_6S_2$ | | | |
| 81 | 3,4-OCH₂O— | Me | H | 1 | 5 | 82 | amorph. | | +105.2 (1.0, MeOH, 25) | $C_{15}H_{17}NO_5S_2$ | | | |

*$C_{12}H_{23}N$ is dicyclohexylamine.
**$C_6H_{12}$ is cyclohexane.

TABLE III

| Compd. No. | R¹ | R⁵ | R² | Method of prepn. (Examp. No.) | Yield (%) | mp. (°C.) | Recrystn. solvent | $[\alpha]_D$ deg. (c, solv., °C.) | Formula | Analysis (%) Calcd. (Found) C | H | N |
|---|---|---|---|---|---|---|---|---|---|---|---|---|
| 82 | 1-naphthyl | Me | COPh | 2 | 75 | amorph. | | −101.0 (1.5, MeOH, 26) | $C_{25}H_{23}NO_4S_2$ | | | |
| 83 | 1-naphthyl | Me | H | 5 | 69 | amorph. | | −202.0 (0.6, MeOH, 26) | $C_{18}H_{19}NO_3S_2$ | | | |
| 84 | 2-furyl | Me | COPh | 2 | 82 | 122–123 | benzene-n-hexane | +45.5 (1.0, MeOH, 25) | $C_{19}H_{19}NO_5S_2$ | 56.28 (56.39) | 4.72 (4.57) | 3.45 (3.36) |
| 85 | 2-furyl | Me | H | 5 | 85 | oil | | +48.8 (1.0, MeOH, 25) | $C_{12}H_{15}NO_4S_2$ | | | |
| 86 | 5-methyl-2-furyl | Me | COPh | 1 | 81 | 125–126 | benzene-n-hexane | +79.9 (1.0, MeOH, 25) | $C_{20}H_{21}NO_5S_2$ | 57.26 (57.62) | 5.05 (5.04) | 3.34 (3.30) |
| 87 | 5-methyl-2-furyl | Me | H | 5 | 79 | oil | | +78.1 (1.0, MeOH, 25) | $C_{13}H_{17}NO_4S_2$ | | | |
| 88 | 2-thienyl | H | COPh | 3 | 57 | 141–143 | benzene | +107.7 (1.0, MeOH, 25) | $C_{18}H_{17}NO_4S_3$ | 53.05 (52.93) | 4.20 (4.01) | 3.44 (3.31) |
| 89 | 2-thienyl | H | H | 5 | 56 | amorph. | | +87.5 (1.0, MeOH, 25) | $C_{11}H_{13}NO_3S_3$ | | | |
| 90 | 2-thienyl | Me | COPh | 4 | 49 | 136–137 | benzene | +79.6 (1.0, MeOH, 25) | $C_{19}H_{19}NO_4S_3$ | 54.14 (54.19) | 4.54 (4.36) | 3.32 (3.26) |
| 91 | 2-thienyl | Me | H | 5 | 42 | amorph. | | +55.7 (1.0, MeOH, 26) | $C_{12}H_{15}NO_3S_3$ | | | |

TABLE III-continued $$R^1 \underset{O}{\overset{S}{\underset{N}{\bigtriangleup}}} \underset{R^5}{\overset{}{\bigtriangleup}} \begin{matrix} CO_2H \\ SR^2 \end{matrix}$$

| Compd. No. | $R^1$ | $R^5$ | $R^2$ | Method of prepn. (Examp. No.) | Yield (%) | mp. (°C.) | Recrystn. solvent | $[\alpha]_D$ deg. (c, solv., °C.) | Formula | Analysis (%) Calcd. (Found) C | H | N |
|---|---|---|---|---|---|---|---|---|---|---|---|---|
| 92 | 3-pyridyl | Me | COPh | 2 | 79 | amorph. | | −59.0 (1.0, MeOH, 25) | $C_{20}H_{20}N_2O_4S_2$ | 57.67 (57.29) | 4.84 (5.49) | 6.73 (6.46) |
| 93 | 3-pyridyl | Me | H | 5 | 83 | amorph. | | −13.5 (1.0, MeOH, 25) | $C_{13}H_{16}N_2O_3S_2$ | | | |
| 94 | 4-pyridyl | Me | COPh | 2 | 60 | amorph. | | −4.4 (1.1, MeOH, 25) | $C_{20}H_{20}N_2O_4S_2$ | | | |
| 95 | 4-pyridyl | Me | H | 5 | 61 | amorph. | | +64.0 (1.0, MeOH, 23) | $C_{13}H_{16}N_2O_3S_2$ | | | |

The potent antihypertensive effect of the compounds of formula I and salts thereof is clear in comparison with that of certain antihypertensive compound as explained below. The inhibitor of angiotensin I-converting enzyme which converts biologically inactive decapeptide, angiotensin I, to active octapeptide, angiotensin II, is found useful as antihypertensive medicine [R. L. Soffer, Annual Review of Biochemistry, 45, 73 (1976); M. A. Ondetti et al., Science, 196, 441 (1977)]. In view of the above, we investigated the pharmacological activities of the compounds of this invention from the aspect of inhibitory activity against the enzyme.

PHARMACOLOGICAL TEST 1

As the method of measurement of angiotensin I-converting enzyme activity, bioassay for the contractile response of isolated smooth muscle or the pressor response of normal animals and biochemical assay for the enzyme isolated from lung or other organs of animals are known. The former is found more advantageous than the latter for the examination of the convertion of angiotensin I to angiotensin II in vivo.

In the present study, therefore, we adopted the bioassay for contractile response of isolated guinea pig ileum to angiotensin I.

Measurement of Inhibitory Activity of Angiotensin I-Converting Enzyme

Isolated guinea pig ileum was suspended in the organ bath containing 20 ml of Tyrode's solution of 30° C. gassed with 95% $O_2$ + 5% $CO_2$. The contraction induced by the addition of angiotensin I (0.1 μg/ml) at intervals of 10 minutes was recorded on a recticorder (Nihon Koden) for 90 seconds using FD pick up (ST-1T-H), Nihon Koden).

The test compounds were added to the bath 5 minutes before the addition of angiotensin I.

The inhibitory activity of angiotensin-I-converting enzyme was calculated by the following formula.

$$(A-B)/A \times 100$$

A: contractile intensity of angiotensin I before addition of the compound

B: contractile intensity of angiotensin I after addition of the compound

From the fact that kininase II, which destroys bradykinin having contractive action on isolated guinea pig ileum, is thought to be identical with angiotensin I-converting enzyme, augmentation of the contractile response to bradykinin by test compounds was examined by using bradykinin (0.005 μg/ml) in place of angiotensin I according to the above mentioned method.

The results are shown in Table IV. All of the test compounds inhibited the contractile response to angiotensin I, while they enhanced the response to bradykinin.

PHARMACOLOGICAL TEST 2

The activity of angiotensin I-converting enzyme was measured by spectrophotometry according to the method of D. W. Cushman and H. S. Cheung [Biochem. Pharmacol., 20, 1637 (1971)]. That is, the absorbance of hippuric acid was measured, which is liberated by incubating hippuryl-L-histidyl-L-leucine (HHL) as substrate in the presence of angiotensin I-converting enzyme extracted from rabbit lung.

Measurement of Inhibitory Activity of Angiotensin I-Converting Enzyme

The reaction mixture is as follows:
100 mM phosphate buffer (pH 8.3)
300 mM sodium chloride
5 mM HHL
$10^{-3} \sim 10^{-9}$ M enzyme inhibitor
5 mU enzyme 0.25 ml of the above mixture was incubated at 37° C. for 30 minutes and the reaction was stopped by adding 0.25 ml of 1 N hydrochloric acid. To this solution, 1.5 ml of ethyl acetate was added in order to extract hippuric acid. 1.0 ml of ethyl acetate layer was collected and evaporated to dryness, and the residue obtained was dissolved in 1.0 ml of water. The absorbance of this solution was measured at 228 nm.

The inhibitory activity of angiotensin I-converting enzyme was calculated by the following formula:

Percent inhibition $= (A - B)/A \times 100$

A: absorbance of reaction solution before addition of the compound
B: absorbance of reaction solution after addition of the compound Concentration of Compound Producing 50% Inhibition of Angiotensin I-Converting Enzyme ($IC_{50}$)

The solution containing compounds at the concentration of $1 \times 10^{-3}$ M to $1 \times 10^{-9}$ M was incubated and percent inhibition at each concentration was calculated according to the above formula, and then $IC_{50}$, concentration of the compound producing 50% inhibition of the enzyme activity, was determined.

The results are shown in Table IV.

PHARMACOLOGICAL TEST 3

Male Wistar strain rats weighing about 200-300 g were used.

Under ether anesthesia, polyethylene cannulae are inserted into carotid arthery and jugular vein. The cannula to carotid artery is connected to an electric transducer, while the cannula to jugular vein is connected to an apparatus for continuous infusion. After the complete recovery from anesthesia, angiotensin I is infused intravenously in a dose of 300 ng/kg by the apparatus for continuous infusion, and the pressor response is recorded by polygraph (Nihon Koden, RM-150).

The compounds of this invention suspended in 0.5% tragacanth solution are administered orally in a dose of 0.3 ml per 100 g of body weight, and the pressor response to angiotensin I infused intravenously is measured with time.

The inhibitory activity of the compounds against angiotensin I-converting enzyme is expressed as the percent inhibition of pressor response to angiotensin I.

Table V shows the changes of percent inhibition of the compounds of this invention with time.

TOXICITY TEST

Acute toxicity of the compounds of this invention is shown in Table VI.

(Experimental Animals)

The male ddy-SLC strain rats (4 weeks of age, weighing 19-21 g) were placed in a breeding room of constant temperature and humidity (23±1° C., 55±5%) and fed freely pellet diet (CE-2, Clea Japan Inc.) and water ad. libitum for a week. The rats showing the normal growth were selected for the experiment.

(Method of Administration)

Test compounds are suspended in 0.5% tragacanth solution (p.o.) or dissolved in distilled water (i.v., i.p.), and administered in a dose of 0.5 ml/20 g body weight.

TABLE IV

Inhibitory activity of the compounds against angiotensin I-converting enzyme

| Compound No. | Angiotensin I $IC_{50}$* [M] | Angiotensin I-converting enzyme $IC_{50}$** [M] | Bradykinin $AC_{50}$*** [M] |
|---|---|---|---|
| 2 | $4.8 \times 10^{-7}$ | $3.2 \times 10^{-6}$ | $1.9 \times 10^{-8}$ |
| 4 | $5.0 \times 10^{-8}$ | $1.2 \times 10^{-7}$ | $2.0 \times 10^{-9}$ |
| 6a | $4.1 \times 10^{-7}$ | $6.5 \times 10^{-7}$ | $1.5 \times 10^{-8}$ |
| 6b | $3.0 \times 10^{-7}$ | $3.7 \times 10^{-7}$ | $3.7 \times 10^{-9}$ |
| 8a | $8.5 \times 10^{-8}$ | $2.5 \times 10^{-7}$ | $1.4 \times 10^{-9}$ |
| 8b | $1.4 \times 10^{-7}$ | $2.9 \times 10^{-7}$ | $1.1 \times 10^{-9}$ |
| 10a | $8.1 \times 10^{-7}$ | $2.8 \times 10^{-6}$ | $1.3 \times 10^{-8}$ |
| 10b | $5.8 \times 10^{-7}$ | $3.1 \times 10^{-7}$ | $1.0 \times 10^{-8}$ |
| 12 | $9.0 \times 10^{-7}$ | $1.3 \times 10^{-5}$ | $1.9 \times 10^{-8}$ |
| 16 | $2.4 \times 10^{-7}$ | $4.5 \times 10^{-7}$ | $2.6 \times 10^{-9}$ |
| 18 | $1.9 \times 10^{-7}$ | $6.0 \times 10^{-8}$ | $3.1 \times 10^{-9}$ |
| 22 | $1.7 \times 10^{-7}$ | $5.4 \times 10^{-7}$ | $3.9 \times 10^{-9}$ |
| 24 | $7.0 \times 10^{-7}$ | $3.6 \times 10^{-6}$ | $1.6 \times 10^{-8}$ |
| 34 | $1.8 \times 10^{-7}$ | $4.0 \times 10^{-7}$ | $2.5 \times 10^{-9}$ |
| 44 | $5.6 \times 10^{-7}$ | $2.2 \times 10^{-6}$ | $5.0 \times 10^{-9}$ |
| 46 | $1.9 \times 10^{-8}$ | $7.0 \times 10^{-8}$ | $3.0 \times 10^{-10}$ |
| 50 | $5.6 \times 10^{-8}$ | $2.2 \times 10^{-7}$ | $7.0 \times 10^{-10}$ |
| 52 | $7.1 \times 10^{-8}$ | $2.1 \times 10^{-7}$ | $1.5 \times 10^{-9}$ |
| 54 | $1.5 \times 10^{-7}$ | $2.3 \times 10^{-7}$ | $1.7 \times 10^{-9}$ |
| 56 | $4.6 \times 10^{-7}$ | $1.2 \times 10^{-6}$ | $5.5 \times 10^{-9}$ |
| 58 | $5.2 \times 10^{-7}$ | $2.6 \times 10^{-6}$ | $5.8 \times 10^{-9}$ |
| 60 | $9.2 \times 10^{-8}$ | $7.5 \times 10^{-8}$ | $2.0 \times 10^{-9}$ |
| 64 | $5.0 \times 10^{-7}$ | $4.2 \times 10^{-7}$ | $8.0 \times 10^{-9}$ |
| 68 | $8.8 \times 10^{-8}$ | $7.5 \times 10^{-7}$ | $2.1 \times 10^{-9}$ |
| 71 | $4.1 \times 10^{-7}$ | $3.9 \times 10^{-7}$ | $9.4 \times 10^{-9}$ |
| 73 | $3.6 \times 10^{-8}$ | $9.3 \times 10^{-8}$ | $1.1 \times 10^{-9}$ |
| 75 | $1.4 \times 10^{-7}$ | $2.0 \times 10^{-7}$ | $3.1 \times 10^{-9}$ |
| 77 | $1.2 \times 10^{-7}$ | $1.9 \times 10^{-7}$ | $1.3 \times 10^{-9}$ |
| 79 | $2.1 \times 10^{-7}$ | $1.3 \times 10^{-6}$ | $3.2 \times 10^{-9}$ |
| 81 | $1.4 \times 10^{-7}$ | $2.4 \times 10^{-7}$ | $9.4 \times 10^{-10}$ |
| 83 | $3.6 \times 10^{-7}$ | $1.3 \times 10^{-6}$ | $1.3 \times 10^{-8}$ |
| 85 | $2.4 \times 10^{-7}$ | $3.4 \times 10^{-7}$ | $3.7 \times 10^{-9}$ |
| 87 | $4.6 \times 10^{-7}$ | $7.3 \times 10^{-7}$ | $2.6 \times 10^{-9}$ |
| 91 | $7.0 \times 10^{-7}$ | $3.7 \times 10^{-7}$ | $1.0 \times 10^{-8}$ |
| 93 | $1.4 \times 10^{-7}$ | $8.4 \times 10^{-7}$ | $2.9 \times 10^{-9}$ |
| 95 | $8.3 \times 10^{-8}$ | $1.1 \times 10^{-7}$ | $3.1 \times 10^{-9}$ |
| 96**** | $1.7 \times 10^{-7}$ | $2.6 \times 10^{-7}$ | $2.6 \times 10^{-9}$ |

*Concentration of compound producing 50% inhibition of angiotensin I activity inducing the contraction of guinea pig ileum.
**Concentration of compound producing 50% inhibition of angiotensin I-converting enzyme.
***Concentration of compound producing 50% augmentation of bradykinin activity inducing the contraction of guinea pig ileum.
****(4R)-3-[(2S)—3-Mercapto-2-methylpropanoyl]-4-thiazolidinecarboxylic acid.

TABLE V

| Compd. No. | Dose (mg/kg) | Inhibition (%) | | | | | | | | | | |
|---|---|---|---|---|---|---|---|---|---|---|---|---|
| | | 5 | 15 | 25 | 35 | 45 | 55 | 65 | 75 | 85 | 95 | 105 | 115 (min.) |
| 3 | 1.8 | 35.2 | 40.8 | 26.9 | 17.9 | 14.2 | 14.8 | 6.3 | 9.5 | 5.8 | | | |

TABLE V-continued

| Compd. No. | Dose (mg/kg) | Inhibition (%) | | | | | | | | | | | (min.) |
|---|---|---|---|---|---|---|---|---|---|---|---|---|---|
| | | 5 | 15 | 25 | 35 | 45 | 55 | 65 | 75 | 85 | 95 | 105 | 115 | |
| 4 | 1.3 | 46.7 | 46.5 | 37.2 | 32.2 | 28.8 | 27.5 | 27.5 | 13.8 | 14.5 | 10.3 | | | |
| 45* | 1.8 | 20.0 | 26.6 | 30.1 | 31.8 | 20.9 | 13.5 | 19.0 | 14.9 | 20.9 | 10.3 | 10.3 | 8.8 | |
| 46 | 1.3 | 53.3 | 62.9 | 64.7 | 63.7 | 54.0 | 49.3 | 47.7 | 38.8 | 34.0 | 30.0 | 30.0 | 31.0 | |
| 49 | 1.8 | 27.8 | 34.4 | 42.9 | 38.5 | 47.7 | 43.7 | 47.0 | 45.6 | 31.6 | 31.7 | 30.4 | 35.0 | |
| 50 | 1.4 | 11.1 | 22.7 | 37.6 | 43.9 | 52.6 | 31.7 | 28.1 | 30.5 | 24.3 | 21.1 | 21.7 | 21.5 | |
| 76 | 2.0 | 26.0 | 45.9 | 56.1 | 55.9 | 58.2 | 47.1 | 48.9 | 40.7 | 41.7 | 32.2 | 30.6 | 28.5 | |
| 77 | 1.5 | 35.0 | 45.0 | 54.2 | 50.8 | 57.2 | 49.2 | 47.8 | 34.8 | 31.7 | 24.2 | 18.7 | 6.7 | |

*solvent free

TABLE VI

| Compound No. | p.o. | i.v. | i.p. |
|---|---|---|---|
| 18 | | | LD > 1000 mg/kg* |
| 46 | LD$_{50}$ > 10000 mg/kg | LD$_{50}$ > 1100-1300 mg/kg* | |

*pH 7

It is found from the above pharmacological tests that the compounds I of this invention are useful as antihypertensive agents. The compounds can be given with the combination of diuretics such as hydroflumethiazide, furosemide, and bumetanide same as other antihypertensive agents. The compounds can be administered either orally or parenterally. The dosage forms are tablet, capsule, granule, powder, suppository, injection, etc. In the treatment of hypertention, these preparations can contain not only general excipients but also other antihypertensive agents such as reserpine, α-methyldopa, guanethidine, clonidine, hydralazine, etc. The dose is adjusted depending on symptom, dosage form, etc. But, usual daily dosage is 1 to 5000 mg, preferably 10 to 1000 mg, in one or a few divided doses.

EXAMPLES OF FORMULATION (1) Oral drug
    a. tablet

| | |
|---|---|
| compound 46 | 30 mg |
| lactose | 150 mg |
| crystalline cellulose | 50 mg |
| calcium carboxymethylcellulose | 7 mg |
| magnesium stearate | 3 mg |
| Total | 240 mg |
| compound 46 | 150 mg |
| lactose | 60 mg |
| crystalline cellulose | 30 mg |
| calcium carboxymethylcellulose | 7 mg |
| magnesium stearate | 3 mg |
| Total | 250 mg |
| compound 49 | 50 mg |
| lactose | 120 mg |
| crystalline cellulose | 60 mg |
| calcium carboxymethylcellulose | 7 mg |
| magnesium stearate | 3 mg |
| Total | 240 mg |
| compound 81 | 100 mg |
| lactose | 95 mg |
| crystalline cellulose | 45 mg |
| calcium carboxymethylcellulose | 7 mg |
| magnesium stearate | 3 mg |
| Total | 250 mg |

The tablets may be treated with the common film-coating and further with sugar-coating.

b. granule

| | |
|---|---|
| compound 46 | 30 mg |
| polyvinylpyrrolidone | 25 mg |
| lactose | 385 mg |
| hydroxypropylcellulose | 50 mg |
| talc | 10 mg |
| Total | 500 mg |
| compound 73 | 150 mg |
| polyvinylpyrrolidone | 20 mg |
| lactose | 280 mg |
| hydroxypropylcellulose | 40 mg |
| talc | 10 mg |
| Total | 500 mg | c. powder

| | |
|---|---|
| compound 46 | 30 mg |
| lactose | 500 mg |
| starch | 440 mg |
| colloidal silica | 30 mg |
| Total | 1000 mg |
| compound 46 | 300 mg |
| lactose | 230 mg |
| starch | 440 mg |
| colloidal silica | 30 mg |
| Total | 1000 mg |
| compound 95 | 250 mg |
| lactose | 240 mg |
| starch | 480 mg |
| colloidal silica | 30 mg |
| Total | 1000 mg | d. capsule

| | |
|---|---|
| compound 46 | 30 mg |
| lactose | 102 mg |
| crystalline cellulose | 56 mg |
| colloidal silica | 2 mg |
| Total | 190 mg |
| compound 50 | 100 mg |
| lactose | 60 mg |
| crystalline cellulose | 38 mg |
| colloidal silica | 2 mg |
| Total | 200 mg |
| compound 22 | 200 mg |
| glycerol | 179.98 mg |
| butyl p-hydroxybenzoate | 0.02 mg |
| Total | 380 mg |
| compound 46 | 30 mg |
| glycerol | 349.98 mg |
| butyl p-hydroxybenzoate | 0.02 mg |
| Total | 380 mg |

(2) Injection
    a. 1 to 30mg of compound 46 is contained in 1ml of the aqueous solution (pH 6.5-7.0).

What we claim is:
1. A compound of the formula

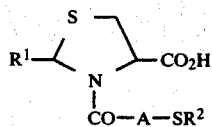

(I)

wherein R¹ is selected from the group consisting of furyl, thienyl, and furyl and thienyl each substituted with at least one substituent selected from the group consisting of lower alkyl, hydroxy, mercapto, lower alkoxy, lower alkylenedioxy, lower alkanoyloxy, benzoyloxy, benzyloxycarbonyloxy, lower alkanoylmercapto, benzoylmercapto, benzyloxycarbonylmercapto, halogen, nitro, amino, lower alkylamino, lower alkanoylamino, benzoylamino or benzyloxycarbonylamino;

R² is hydrogen or benzoyl;

A is straight or branched alkylene of 1 to 3 carbon atoms; and pharmaceutically acceptable salts thereof; wherein the terms lower alkyl, lower alkoxy, lower alkylene and lower alkanoyl refer to groups having 1 to 6 carbon atoms.

2. A compound as in claim 1 wherein R¹ is 2-furyl, 2-(5-methyl)furyl or 2-thienyl.

3. A compound as in claim 1 or 2 wherein R² is hydrogen or benzoyl.

4. A compound as in claim 1 wherein A is —CH₂—, —CH(CH₃)—, —CH₂CH₂— or —CH(CH₃)CH₂—.

5. (4R)-3-(S-benzoyl-3-mercapto-2-methylpropanoyl)-2-(2-furyl)-4-thiazolidinecarboxylic acid of the formula of claim 1.

6. (4R)-2-(2-furyl)-3-(3-mercapto-2-methylpropanoyl)-4-thiazolidinecarboxylic acid of the formula of claim 1.

7. (4R)-3-(S-benzoyl-3-mercapto-2-methylpropanoyl)-2-(2-thienyl)-4-thiazolidinecarboxylic acid of the formula of claim 1.

8. (4R)-3-(3-mercapto-2-methylpropanoyl)-2-(2-thienyl-4-thiazolidine carboxylic acid of the formula of claim 1.

9. A composition comprising a compound of any of claims 1, 2, 3, 4, 5, 6, 7 or 8 in an amount sufficient to reduce blood pressure and pharmaceutically acceptable excipient(s).

10. A method for reducing blood pressure which comprises administering a composition comprising a compound of any of claims 1, 2, 3, 4, 5, 6, 7 or 8 and pharmaceutically acceptable excipient(s).

11. The compounds of claim 1 or 12 wherein A is —CH₂CH₂—.

12. The compounds of claim 3 wherein A is —CH₂CH₂—.

13. The compounds of claim 1 or 2 wherein A is —CH(CH₃)CH₂—.

14. The compounds of claim 3 wherein A is —CH(CH₃)CH₂—.

15. (4R)-3-(S-benzoyl-3-mercapto-2-methylpropanoyl)-2-[2-(5-methyl)furyl]-4-thiazolidinecarboxylic acid of the formula of claim 1.

16. (4R)-3-(3-mercapto-2-methylpropanoyl)-2-[2-(5-methyl)furyl]-4-thiazolidinecarboxylic acid of the formula of claim 1.

17. (4R)-3-(S-benzoyl-3-mercaptopropanoyl)-2-(2-thienyl)-4-thiazolidinecarboxylic acid of the formula of claim 1.

18. (4R)-3-(3-mercaptopropanoyl)-2-(2-thienyl)-4-thiazolidinecarboxylic acid of the formula of claim 1.

19. The compounds of claim 1 wherein R¹ is selected from the group consisting of furyl, thienyl, and furyl and thienyl each substituted with at least one substituent selected from the group consisting of lower alkyl, hydroxy, lower alkoxy, lower alkanoyloxy, benzoyloxy, benzyloxycarbonyloxy, halogen, nitro, amino, lower alkylamino, benzoylamino or benzyloxycarbonylamino.

* * * * *

UNITED STATES PATENT AND TRADEMARK OFFICE
CERTIFICATE OF CORRECTION

PATENT NO. : 4,386,096

DATED : May 31, 1983

INVENTOR(S) : Junichi IWAO et al

It is certified that error appears in the above-identified patent and that said Letters Patent is hereby corrected as shown below:

Column 4, line 60: replace "1620" with --1626--.

Column 26, line 8: delete "3,".

Column 26, line 13: delete "3,".

Signed and Sealed this

Twenty-seventh Day of March 1984

[SEAL]

Attest:

GERALD J. MOSSINGHOFF

Attesting Officer — Commissioner of Patents and Trademarks